US011353606B2

(12) United States Patent
Miyajima et al.

(10) Patent No.: US 11,353,606 B2
(45) Date of Patent: Jun. 7, 2022

(54) RADIATION IMAGE PROCESSING APPARATUS AND RADIATION IMAGE PROCESSING METHOD

(71) Applicant: Shimadzu Corporation, Kyoto (JP)

(72) Inventors: Takahiro Miyajima, Kyoto (JP); Junya Yamamoto, Kyoto (JP); Kazuyoshi Nishino, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/530,132

(22) Filed: Aug. 2, 2019

(65) Prior Publication Data

US 2020/0064502 A1 Feb. 27, 2020

(30) Foreign Application Priority Data

Aug. 2, 2018 (JP) .............................. JP2018-145986

(51) Int. Cl.
*G01T 7/00* (2006.01)
*G06T 7/73* (2017.01)
*A61B 6/00* (2006.01)

(52) U.S. Cl.
CPC .............. *G01T 7/005* (2013.01); *A61B 6/584* (2013.01); *G06T 7/74* (2017.01); *G06T 2207/30204* (2013.01)

(58) Field of Classification Search
CPC . G01T 7/005; G06T 2207/30204; G06T 7/73; G06T 7/74; G06T 7/0012; G06T 2207/10116; A61B 6/583; A61B 6/584; A61B 6/547
See application file for complete search history.

(56) References Cited

U.S. PATENT DOCUMENTS

| | | | | |
|---|---|---|---|---|
| 2004/0252811 A1* | 12/2004 | Morita | ................... | A61B 6/583 378/207 |
| 2004/0264648 A1* | 12/2004 | Claus | ....................... | G06T 7/73 378/163 |
| 2005/0094771 A1* | 5/2005 | Basu | ...................... | A61B 6/032 378/207 |
| 2005/0147206 A1* | 7/2005 | Skalli | ...................... | A61B 6/583 378/41 |
| 2007/0122020 A1* | 5/2007 | Claus | .................... | G06T 11/005 382/131 |
| 2009/0208074 A1* | 8/2009 | Wiersma | ................. | G06T 7/251 382/128 |

(Continued)

FOREIGN PATENT DOCUMENTS

JP 2006181252 A 7/2006

*Primary Examiner* — Dani Fox
*Assistant Examiner* — Soorena Kefayati
(74) *Attorney, Agent, or Firm* — Muir Patent Law, PLLC

(57) ABSTRACT

A radiation image processing apparatus includes: a group processing unit classifying a plurality of metal markers into a first group relatively far from a detector and a second group relatively close to the detector based on the area of each image of the plurality of metal markers in a captured image; a marker classification unit classifying the plurality of metal markers based on the relative positions of the plurality of metal markers to on the image plane of the captured image for each of the classified groups; and a pair processing unit selecting the metal markers of the first group and the metal markers of the second group, of which the relative positions match each other, as a pair.

8 Claims, 6 Drawing Sheets

(56) References Cited

U.S. PATENT DOCUMENTS

| | | | |
|---|---|---|---|
| 2010/0046718 A1* | 2/2010 | Weiser | G06T 7/73 |
| | | | 378/163 |
| 2010/0239144 A1* | 9/2010 | Fichtinger | A61N 5/1027 |
| | | | 382/131 |
| 2011/0123080 A1* | 5/2011 | Sebok | G06T 7/33 |
| | | | 382/131 |
| 2011/0123084 A1* | 5/2011 | Sebok | G06T 7/0012 |
| | | | 382/132 |
| 2012/0281808 A1* | 11/2012 | Graumann | A61B 6/584 |
| | | | 378/41 |
| 2013/0006093 A1* | 1/2013 | Raleigh | A61B 6/584 |
| | | | 600/407 |
| 2013/0094742 A1* | 4/2013 | Feilkas | A61B 6/584 |
| | | | 382/131 |
| 2013/0188782 A1* | 7/2013 | Hannemann | G01B 11/272 |
| | | | 378/207 |
| 2013/0229495 A1* | 9/2013 | Bani-Hashemi | A61B 6/582 |
| | | | 348/46 |
| 2014/0050375 A1* | 2/2014 | Baker | A61B 34/20 |
| | | | 382/128 |
| 2015/0204989 A1* | 7/2015 | Ni | A61B 6/582 |
| | | | 378/207 |
| 2017/0000581 A1* | 1/2017 | Tokuda | G06K 9/6218 |
| 2018/0296176 A1* | 10/2018 | Sra | A61B 6/503 |
| 2019/0001156 A1* | 1/2019 | Tulik | A61N 5/1081 |
| 2019/0142359 A1* | 5/2019 | Zhang | A61B 34/20 |
| | | | 606/130 |
| 2021/0192735 A1* | 6/2021 | Wang | G06T 7/62 |

* cited by examiner

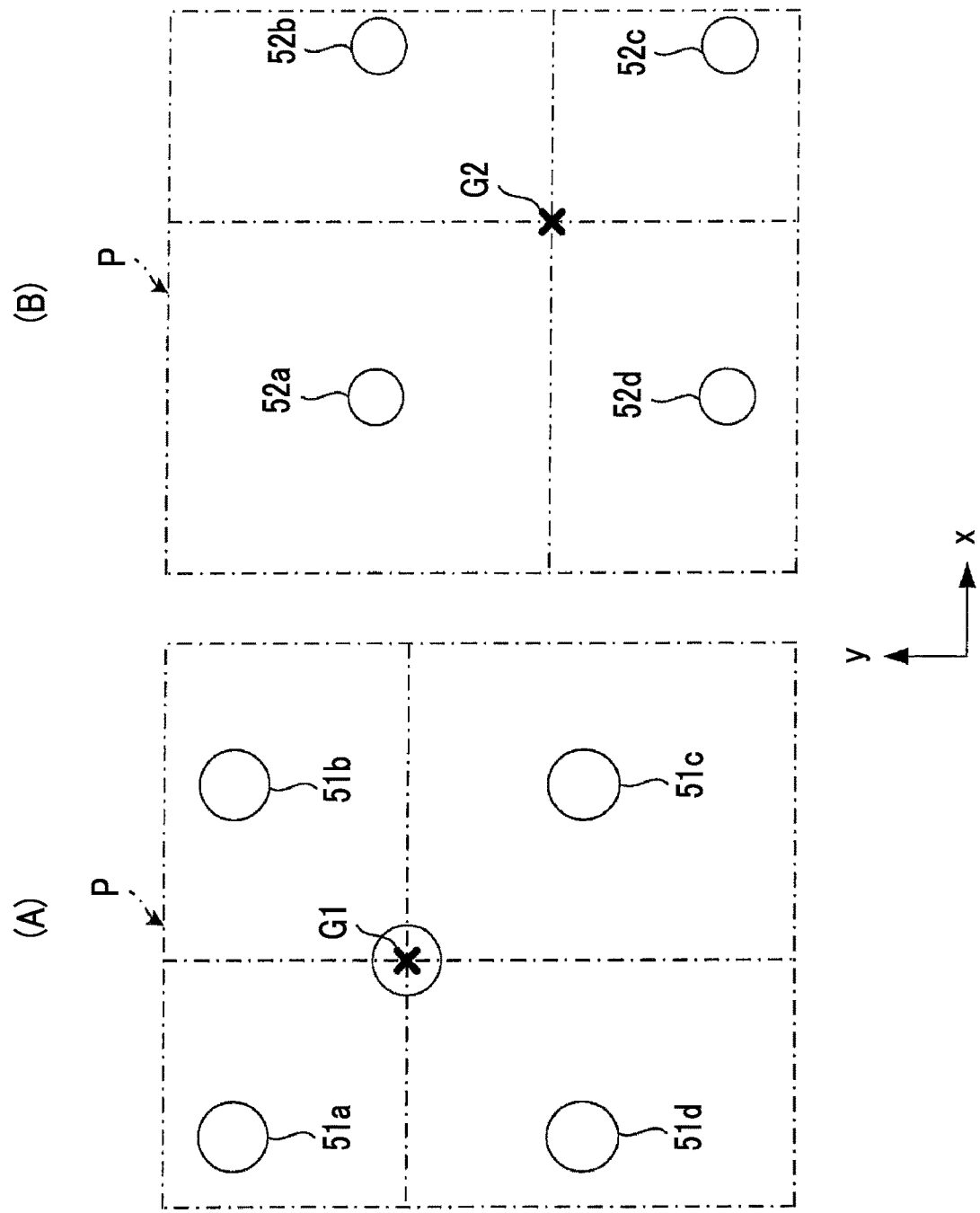

S: (x, y, Sd)
M1: (Pa, Pb, Pd+Ps)
M2: (Pa, Pb, Pd)
I1: (a1, b1, 0)
I2: (a2, b2, 0)

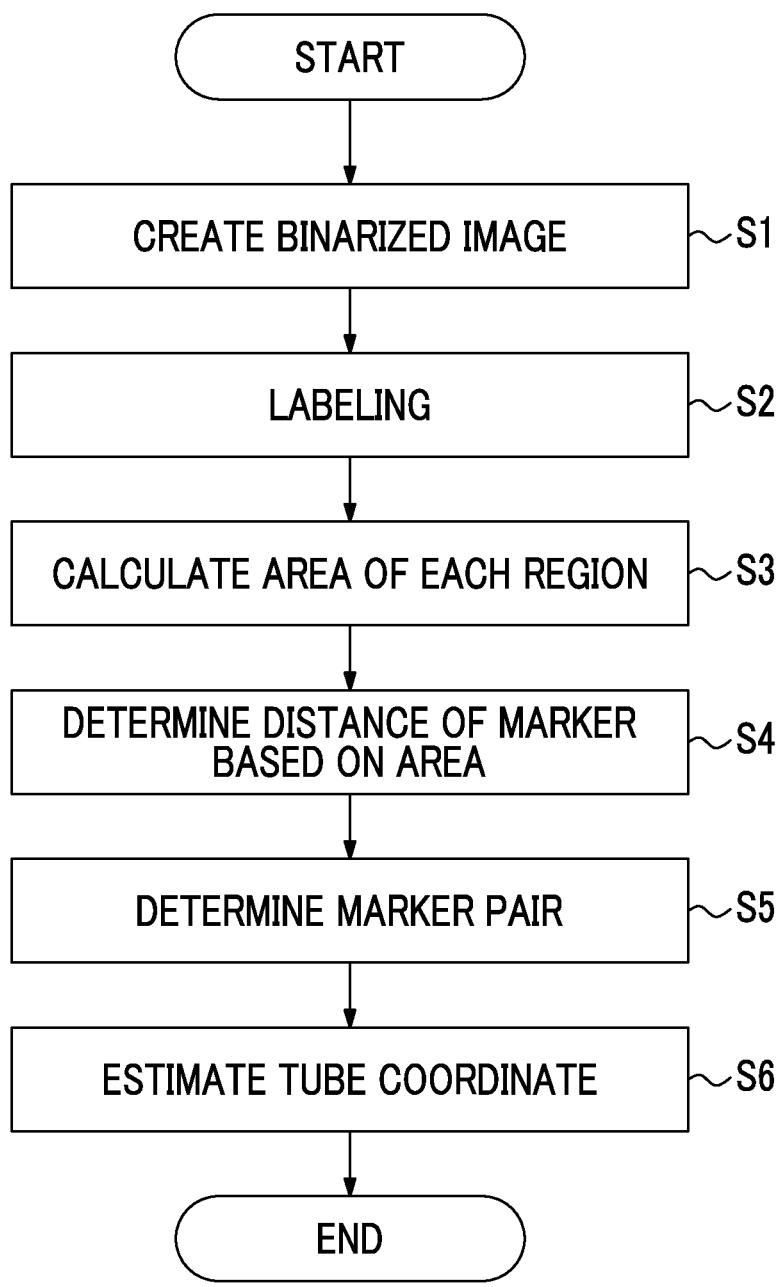

RADIATION IMAGE PROCESSING APPARATUS AND RADIATION IMAGE PROCESSING METHOD

RELATED APPLICATIONS

The contents of Japanese Patent Application No. 2018-145986, on the basis of which priority benefits are claimed in an accompanying application data sheet, is in its entirety incorporated herein by reference.

BACKGROUND OF THE INVENTION

Field of the Invention

The present invention relates to a radiation image processing apparatus and a radiation image processing method for estimating the position of a tube that is a radiation source.

Background Art

A radiation image that performs tomosynthesis acquires signals of a plurality of images by performing imaging while changing the position of a tube that is a radiation source. The radiation image capturing apparatus images a phantom having a pair of metal markers together with a subject, and estimates the position of a tube at the time of imaging based on the position of one pair of metal markers shown in the image (for example, JP-A-2006-181252).

SUMMARY OF THE INVENTION

In a configuration in which the tube position is estimated based on the position of one pair of metal markers as in the known radiation image capturing apparatus described in JP-A-2006-181252, a situation may occur in which the metal markers do not appear in the captured image due to the top plate on which the subject is placed being inclined or the like. As a result, there is a problem that the position of the tube at the time of imaging cannot be accurately estimated.

The present invention has been made in view of the above problem, and it is an object of the present invention to provide a radiation image processing apparatus and a radiation image processing method capable of accurately estimating the position of a tube at the time of imaging.

In order to achieve the aforementioned object, a radiation image processing apparatus in the present invention includes: a detector that is disposed so as to face a tube, which is a movably held radiation source, and converts a captured image by radiation emitted from the tube into image data; a phantom that is provided between the tube and the detector and that has a plurality of markers as a first group at positions relatively far from the detector and has a plurality of markers as a second group at positions relatively close to the detector; determination means for determining whether a plurality of markers in the captured image correspond to markers in the first group or markers in the second group based on an area of each image of the plurality of markers in the captured image; and pair processing means for selecting a marker of the first group and a marker of the second group as a pair based on a relative positional relationship between a plurality of markers in the first and second groups determined by the determination means.

Since the radiation image processing apparatus according to the present invention includes the determination means and the pair processing means described above, a plurality of markers in the captured image can be selected as a pair after being separated in the distance direction with respect to the detector. Therefore, by estimating the position of the tube at the time of imaging based on the positions of the markers selected as a pair from the plurality of markers in the captured image, it is possible to appropriately select a pair, for example, even in a case where the phantom is inclined. As a result, it is possible to correctly estimate the position of the tube at the time of imaging.

Preferably, the radiation image processing apparatus described above further includes tube position estimation processing means for estimating a position of the tube based on position coordinates of markers selected as a pair by the pair processing means. Therefore, it is possible to accurately estimate the position of the tube at the time of imaging. Preferably, by using a central point of a region surrounded by a marker located in an outermost portion in one direction on an image plane of the captured image and a metal marker located in an outermost portion in a direction perpendicular to the one direction as a center of gravity, the plurality of markers are classified based on a position from the center of gravity. Therefore, it is possible to select a pair even in a case where parts of images of the plurality of markers are missing in the captured image. Preferably, the plurality of markers are a number of markers capable of forming at least two pairs from the markers of the first group and the markers of the second group. This enables pair selection with a minimum of markers.

A radiation image processing method in the present invention is a radiation image processing method in a radiation image processing apparatus including a detector that is disposed so as to face a tube, which is a movably held radiation source, and converts a captured image by radiation emitted from the tube into image data and a phantom that is provided between the tube and the detector and that has a plurality of markers as a first group at positions relatively far from the detector and has a plurality of markers as a second group at positions relatively close to the detector. The radiation image processing method includes; a determination step of determining whether a plurality of markers in the captured image correspond to markers in the first group or markers in the second group based on an area of each image of the plurality of markers in the captured image; and a pair processing step of selecting a marker of the first group and a marker of the second group as a pair based on a relative positional relationship between a plurality of markers in the first and second groups determined in the determination step.

In the radiation image processing method according to the present invention, a plurality of markers in the captured image can be selected as a pair after being separated in the distance direction with respect to the detector. Therefore, by estimating the position of the tube at the time of imaging based on the positions of the markers selected as a pair from the plurality of markers in the captured image, it is possible to appropriately select a pair, for example, even in a case where the phantom is inclined. As a result, it is possible to correctly estimate the position of the tube at the time of imaging.

Preferably, the radiation image processing method described above further includes a tube position estimation step of estimating a position of the tube based on position coordinates of markers selected as a pair in the pair processing step. Therefore, it is possible to accurately estimate the position of the tube at the time of imaging. Preferably, by using a central point of a region surrounded by a marker located in an outermost portion in one direction on an image plane of the captured image and a metal marker located in an outermost portion in a direction perpendicular to the one direction as a center of gravity, the plurality of markers are classified based on a position from the center of gravity. Therefore, it is possible to select a pair even in a case where parts of images of the plurality of markers are missing in the captured image. Preferably, the plurality of markers are a number of markers capable of forming at least two pairs from the markers of the first group and the markers of the second group. This enables pair selection with a minimum of markers.

According to the present invention, it is possible to accurately estimate the position of the tube at the time of imaging.

BRIEF DESCRIPTION OF THE DRAWINGS

FIG. 5 is a schematic diagram illustrating marker classification of marker classification means provided in the radiation image processing apparatus.

FIG. 7 is a flowchart illustrating the flow of processing of the radiation image processing apparatus.

DETAILED DESCRIPTION OF THE INVENTION

Hereinafter, an embodiment of the present invention will be described with reference to the diagrams.

A radiation image capturing apparatus 1 including a radiation image processing apparatus 6 according to an embodiment of the present invention will be described with reference to FIGS. 1 to 7.

Figure 1:
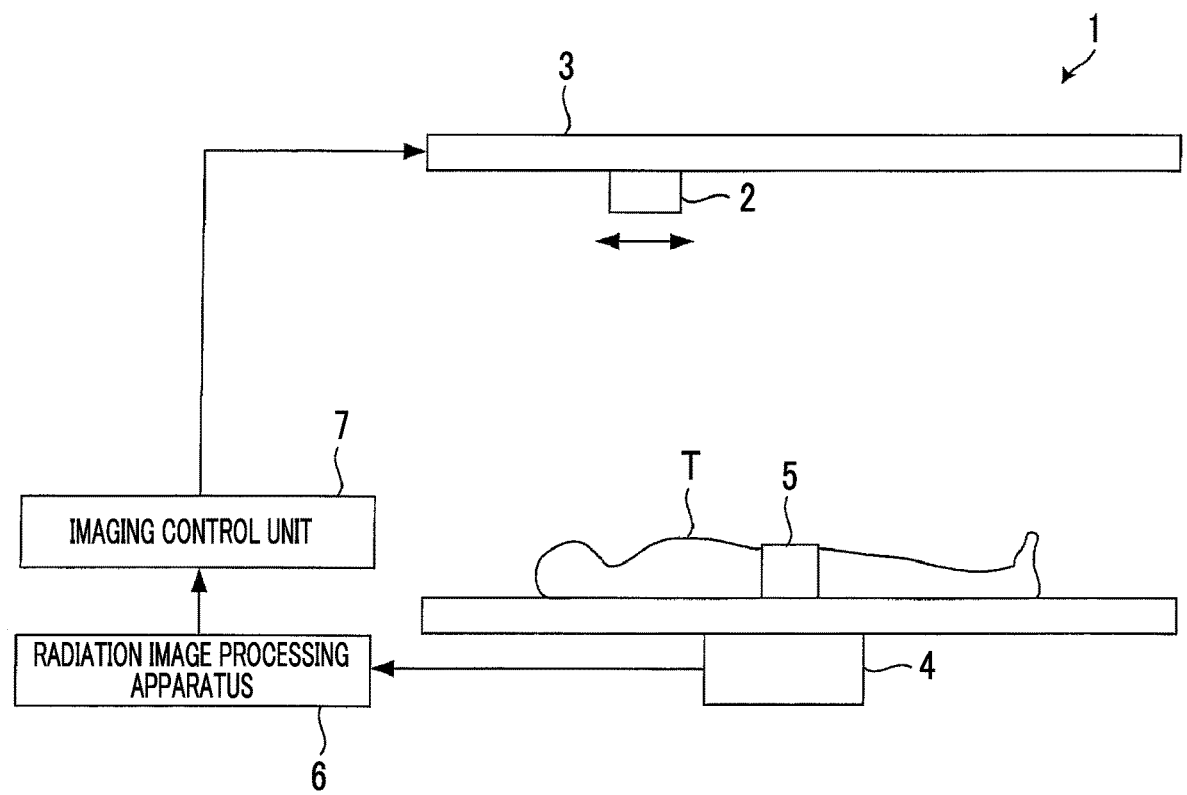
FIG. 1 is a schematic diagram showing the overall configuration of a radiation image capturing apparatus including a radiation image processing apparatus according to an embodiment of the present invention.
Figure 2:
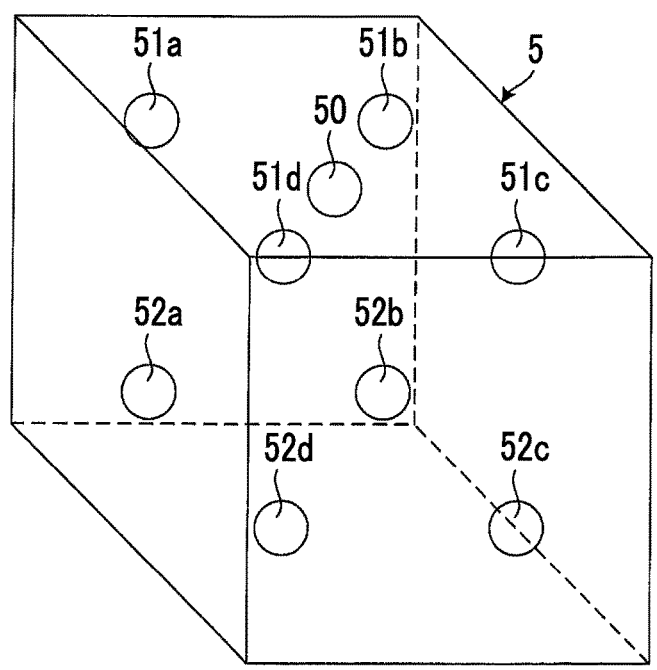
FIG. 2 is a schematic diagram showing a phantom provided in the radiation image capturing apparatus.
Figure 3:
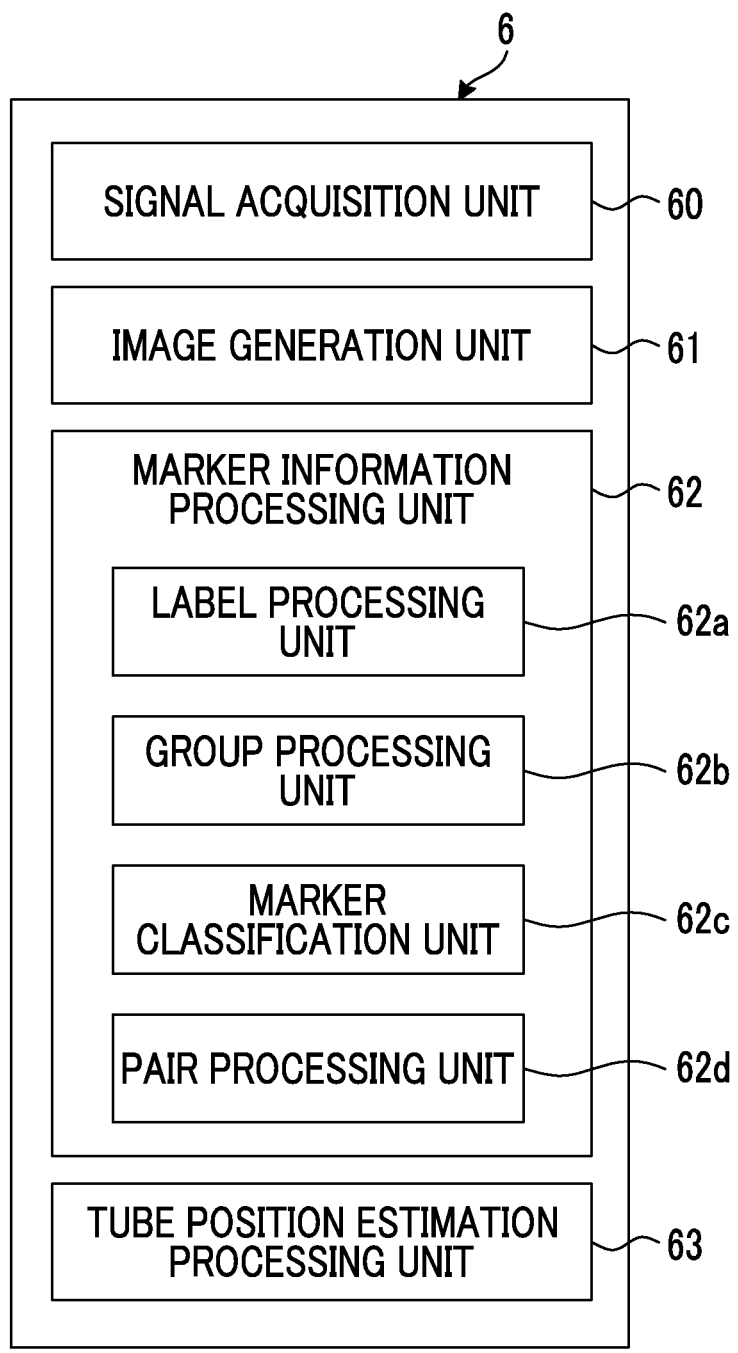
FIG. 3 is a block diagram showing the functional configuration of the radiation image processing apparatus.

First, with reference to FIGS. 1 to 3, the configuration of the radiation image capturing apparatus 1 including the radiation image processing apparatus 6 according to the embodiment of the present invention will be described. FIG. 1 is a schematic diagram showing the overall configuration of the radiation image capturing apparatus 1 including the radiation image processing apparatus 6. FIG. 2 is a schematic diagram showing a phantom 5 provided in the radiation image capturing apparatus 1. FIG. 3 is a block diagram showing the functional configuration of the radiation image processing apparatus 6.

The radiation image capturing apparatus 1 shown in FIG. 1 is an apparatus that performs tomosynthesis for medical purpose, and acquires a plurality of pieces of image data by imaging a subject T while changing the position of a tube 2 that is a radiation source. Specifically, the radiation image capturing apparatus 1 includes the tube 2, a position change mechanism 3, a detector 4, the phantom 5, the radiation image processing apparatus 6, an imaging control unit 7, and the like.

The tube 2 generates radiation (X-rays) by applying a high voltage based on a signal from the imaging control unit 7, and emits the radiation to the detector 4. The tube 2 is movably held by the position change mechanism 3. The position change mechanism 3 changes the position of the tube 2 based on the signal from the imaging control unit 7.

The detector 4 is a flat panel detector (FPD) that is disposed so as to face the tube 2 and converts a captured image by the radiation emitted from the tube 2 into image data. That is, the detector 4 converts the radiation into an electrical signal, reads the converted electrical signal as a signal of an image, and outputs the signal of the image to the radiation image processing apparatus 6. The detector 4 includes a plurality of conversion elements (not shown) and pixel electrodes (not shown) disposed on the plurality of conversion elements. The plurality of conversion elements and the pixel electrodes are disposed at predetermined intervals (pixel pitches).

The phantom 5 is provided between the tube 2 and the detector 4, and is imaged together with the subject T in order to estimate the position of the tube 2. As shown in FIG. 2, the phantom 5 is formed of resin or the like, and has a plurality of metal markers 50, 51$a$, 51$b$, 51$c$, 51$d$, 52$a$, 52$b$, 52$c$, and 52$d$ formed of metal, such as aluminum, gold, lead, and tungsten, thereinside. The metal marker 51$a$ and the metal marker 52$a$ are disposed so as to be separated in a distance direction with respect to the detector 4, thereby forming a pair. The metal marker 51$b$ and the metal marker 52$b$ are disposed so as to be separated in a distance direction with respect to the detector 4, thereby forming a pair. The metal marker 51$c$ and the metal marker 52$c$ are disposed so as to be separated in a distance direction with respect to the detector 4, thereby forming a pair. The metal marker 51$d$ and the metal marker 52$d$ are disposed so as to be separated in a distance direction with respect to the detector 4, thereby forming a pair.

Here, the metal markers forming a pair are disposed so as to be separated from each other by at least 70 mm in the distance direction. In addition, the metal markers forming a pair are disposed at positions that do not overlap each other from the distance direction (in a plan view of the phantom 5).

The explanation will be given by referring back to FIG. 1. The radiation image processing apparatus 6 is an apparatus for processing the signal of the image obtained by the detector 4. The radiation image processing apparatus 6 has a processor (not shown), such as a central processing unit (CPU), a graphics processing unit (GPU), or a field-programmable gate array (FPGA) configured for image processing.

As shown in FIG. 3, the radiation image processing apparatus 6 realizes various functions of a signal acquisition unit 60, an image generation unit 61, a marker information processing unit 62, a tube position estimation processing unit 63, and the like by executing a radiation image processing program.

The signal acquisition unit 60 acquires a signal of an image, which is obtained by the detector 4 (refer to FIG. 1) and in which the subject T and the phantom 5 are imaged, and outputs the acquired signal of the image to the image generation unit 61.

Figure 4A:
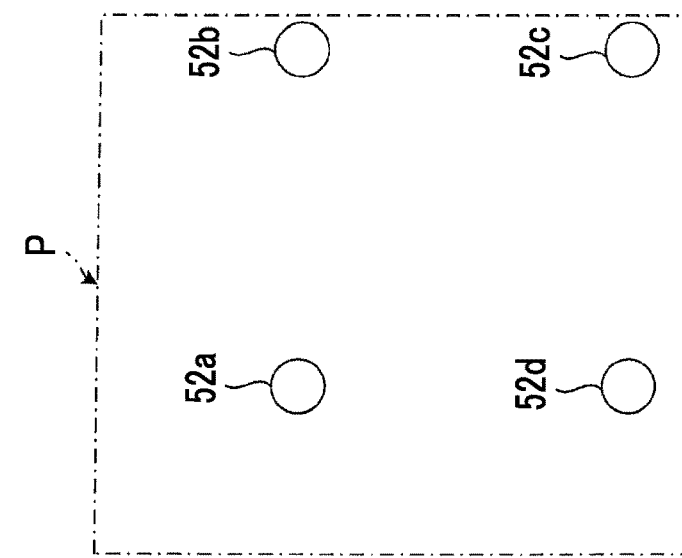
FIGS. 4A to 4C are schematic diagrams illustrating group processing of group processing means provided in the radiation image processing apparatus.
Figure 4B:
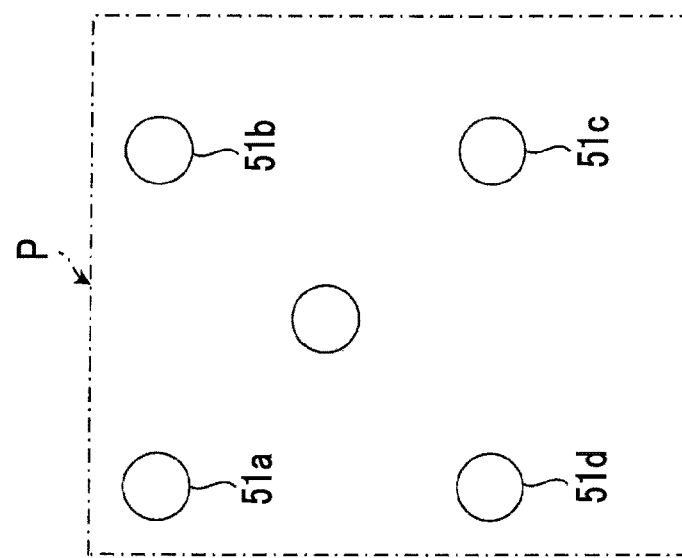
Figure 4C:
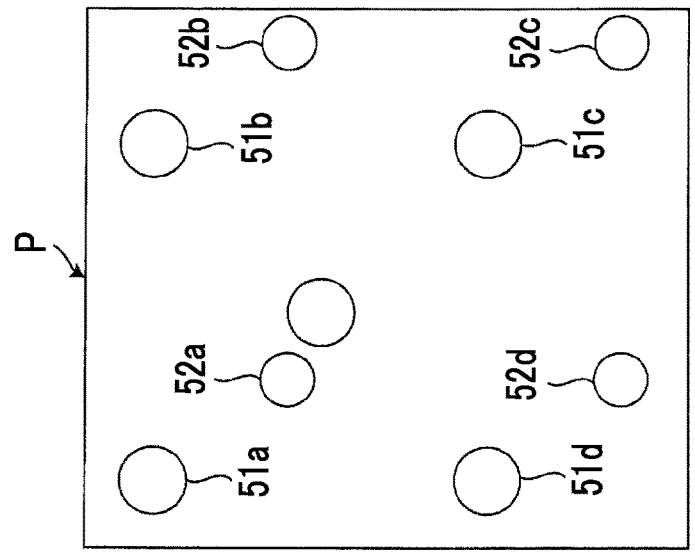

Based on the signal of the image output from the signal acquisition unit 60, the image generation unit 61 generates, for example, a captured image P (refer to FIG. 4A) that is binarized based on a predetermined threshold value of the pixel value. FIG. 4A shows a state in which nine metal markers are drawn in the captured image P, and the drawing of the subject T is omitted.

The marker information processing unit 62 processes the information of the metal markers 51a to 51d and 52a to 52d (refer to FIG. 4A) in the captured image P (refer to FIG. 4A) generated by the image generation unit 61 by image recognition. Specifically, the marker information processing unit 62 includes a label processing unit 62a, a group processing unit 62b, a marker classification unit 62c, a pair processing unit 62d, and the like.

The label processing unit 62a performs labeling processing on each of the plurality of metal markers 51a to 51d and 52a to 52d (refer to FIG. 4A) in the captured image P (refer to FIG. 4A) so that the image of each metal marker and the other images are distinguished from each other.

Based on the area of each of the metal markers 51a to 51d and 52a to 52d (refer to FIG. 4A) in the captured image P labeled by the label processing unit 62a, the group processing unit 62b classifies the metal markers 51a to 51d and 52a to 52d (refer to FIG. 4A) in the captured image P into a first group that is relatively far from the detector 4 (refer to FIG. 1) and a second group that is relatively close to the detector 4 (refer to FIG. 1).

Specifically, the group processing unit 62b calculates the area of each of the metal markers 51a to 51d and 52a to 52d (refer to FIG. 4A) in the captured image P, and then calculates an average value of the maximum value and the minimum value of the calculated area. Then, the group processing unit 62b determines that the metal markers 51a to 51d (refer to FIG. 4B) each having an area larger than the average value, in the captured image P, are relatively far (located in an upper portion within the phantom 5) from the detector 4 (refer to FIG. 1) and classifies the metal markers 51a to 51d (refer to FIG. 4B) into a first group, and determines that the metal markers 52a to 52d (refer to FIG. 4C) each having an area smaller than the average value, in the captured image P, are relatively close (located in a lower portion within the phantom 5) to the detector 4 (refer to FIG. 1) and classifies the metal markers 52a to 52d (refer to FIG. 4C) into a second group.

For each of the classified groups, the marker classification unit 62c classifies the plurality of metal markers 51a to 51d (refer to (A) of FIG. 5) and the plurality of metal markers 52a to 52d (refer to (B) of FIG. 5) based on the relative positions of the plurality of metal markers 51a to 51d (refer to (A) of FIG. 5) and the plurality of metal markers 52a to 52d (refer to (B) of FIG. 5) on the image plane of the captured image P.

Specifically, by using the central point of a region surrounded by a metal marker located in an outermost portion in one direction (x direction) on the image plane of the captured image P (refer to (A) of FIG. 5) and a metal marker located in an outermost portion in a direction (y direction) perpendicular to the one direction (region surrounded by the metal markers 51a to 51d) as a center of gravity G1 (refer to (A) of FIG. 5) of the coordinates of the metal markers 51a to 51d (refer to (A) of FIG. 5) of the first group, the marker classification unit 62c classifies the metal markers 51a to 51d (refer to (A) of FIG. 5) of the first group based on the position from the center of gravity G1 (refer to (A) of FIG. 5).

As shown in (A) of FIG. 5, the metal marker 51a is classified into a metal marker located on the upper left from the center of gravity G1 of the coordinates. The metal marker 51b is classified into a metal marker located on the upper right from the center of gravity G1 of the coordinates. The metal marker 51c is classified into a metal marker located on the lower right from the center of gravity G1 of the coordinates. The metal marker 51d is classified into a metal marker located on the lower left from the center of gravity G1 of the coordinates.

The explanation will be given by referring back to FIG. 3. By using the central point of a region surrounded by a metal marker located in an outermost portion in one direction (x direction) on the image plane of the captured image P (refer to (B) of FIG. 5) and a metal marker located in an outermost portion in a direction (y direction) perpendicular to the one direction (region surrounded by the metal markers 52a to 52d) as a center of gravity G2 (refer to (B) of FIG. 5) of the coordinates of the metal markers 52a to 52d (refer to (B) of FIG. 5) of the second group, the marker classification unit 62c classifies the metal markers 52a to 52d (refer to (B) of FIG. 5) of the second group based on the position from the center of gravity G2 (refer to (B) of FIG. 5).

As shown in (B) of FIG. 5, the metal marker 52a is classified into a metal marker located on the upper left from the center of gravity G2 of the coordinates. The metal marker 52b is classified into a metal marker located on the upper right from the center of gravity G2 of the coordinates. The metal marker 52c is classified into a metal marker located on the lower right from the center of gravity G2 of the coordinates. The metal marker 52d is classified into a metal marker located on the lower left from the center of gravity G2 of the coordinates.

The explanation will be given by referring back to FIG. 3. The pair processing unit 62d selects the metal markers 51a to 51d (refer to (A) of FIG. 5) of the first group and the metal markers 52a to 52d (refer to (B) of FIG. 5) of the second group, of which the relative positions match each other, as a pair.

Specifically, the pair processing unit 62d selects the metal marker 51a (refer to (A) of FIG. 5) located on the upper left from the center of gravity G1 (refer to (A) of FIG. 5) of the coordinates and the metal marker 52a (refer to (B) of FIG. 5) located on the upper left from the center of gravity G2 (refer to (B) of FIG. 5) of the coordinates as a pair. Then, the pair processing unit 62d selects the metal marker 51b (refer to (A) of FIG. 5) located on the upper right from the center of gravity G1 (refer to (A) of FIG. 5) of the coordinates and the metal marker 52b (refer to (B) of FIG. 5) located on the upper right from the center of gravity G2 (refer to (B) of FIG. 5) of the coordinates as a pair.

In addition, the pair processing unit 62d selects the metal marker 51c (refer to (A) of FIG. 5) located on the lower right from the center of gravity G1 (refer to (A) of FIG. 5) of the coordinates and the metal marker 52c (refer to (B) of FIG. 5) located on the lower right from the center of gravity G2 (refer to (B) of FIG. 5) of the coordinates as a pair. In addition, the pair processing unit 62d selects the metal marker 51d (refer to (A) of FIG. 5) located on the lower left from the center of gravity G1 (refer to (A) of FIG. 5) of the coordinates and the metal marker 52d (refer to (B) of FIG. 5) located on the lower left from the center of gravity G2 (refer to (B) of FIG. 5) of the coordinates as a pair.

The tube position estimation processing unit 63 estimates the position of the tube 2 (refer to FIG. 1) based on the position coordinates of the metal markers 51a to 51d (refer to (A) of FIG. 5) and 52a to 52d (refer to (B) of FIG. 5) selected as a pair by the pair processing unit 62d. The position coordinates of each metal marker are set with the center of the FPD (detector 4) as a reference of the coordinates, for example.

Figure 6A:
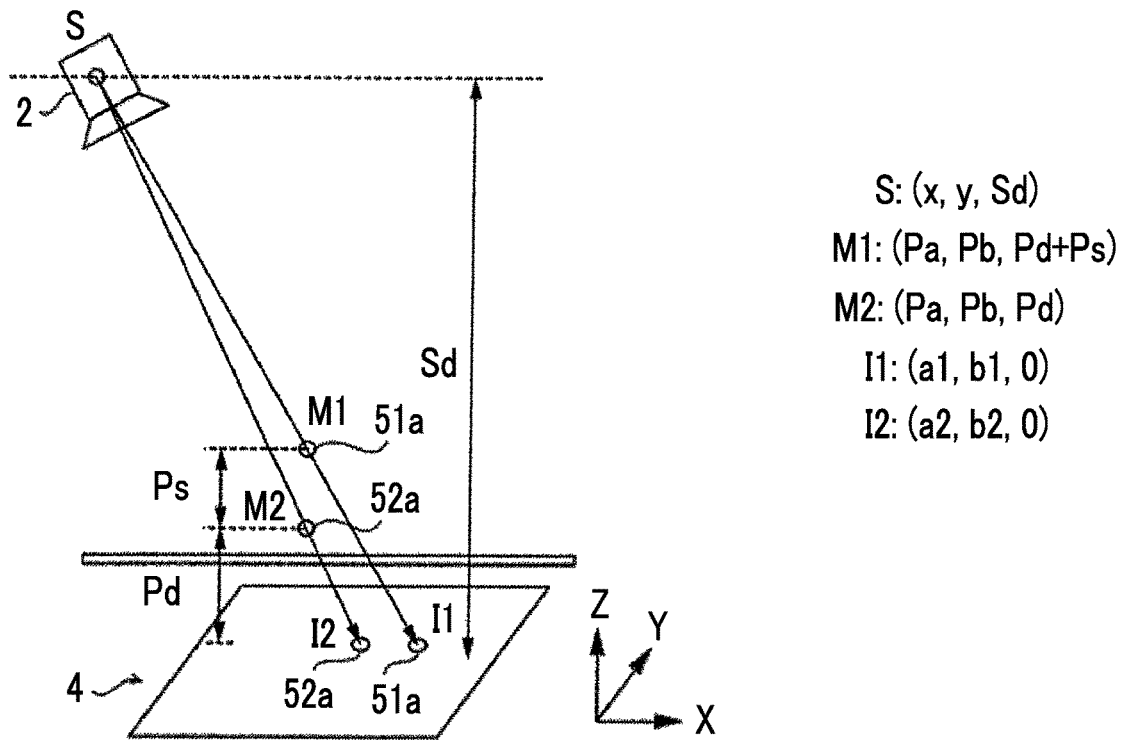
FIGS. 6A to 6C are schematic diagrams illustrating processing for acquiring the position of a tube in the radiation image processing apparatus.
Figure 6B:
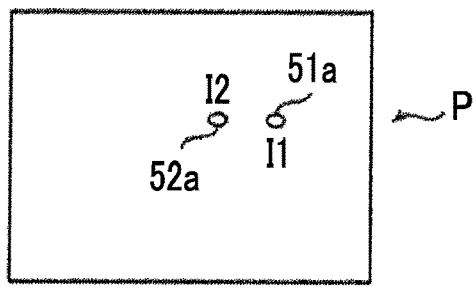
Figure 6C:
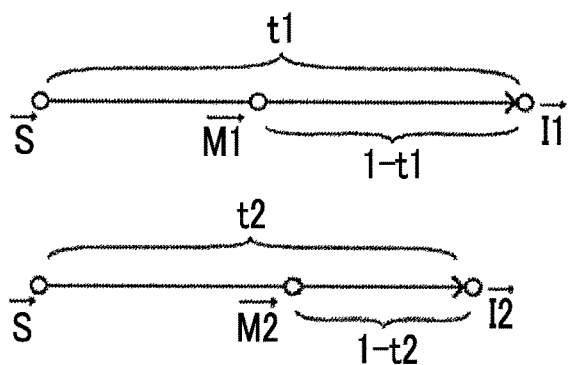

Next, with reference to FIGS. 6A to 6C, processing for acquiring the position information of the tube 2 will be described by taking the metal markers 51a and 52a forming a pair as an example. FIG. 6A is a schematic diagram showing the positional relationship between the tube 2 and the metal markers 51a and 52a. FIG. 6B is a schematic diagram of the captured image P. FIG. 6C is an example showing the positional relationship between the tube 2, the metal markers 51a and 52a, and the metal markers 51a and 52a in the captured image P in a vector diagram. In FIG. 6A, the phantom 5 is not shown for convenience.

As shown in FIG. 6A, in a case where the tube 2 is disposed at a predetermined position so that radiation is emitted from an oblique direction, the radiation transmitted through the metal marker 51a and the metal marker 52a reaches different points on the detector 4. Therefore, as shown in FIG. 6B, the metal markers 51a and 52a in the captured image P are drawn at different positions. Assuming that the position of the tube 2 is S, the position of the metal marker 51a is M1, the position of the metal marker 52a is M2, the position of the metal marker 51a in the captured image P is I1, and the position of the metal marker 52a in the captured image P is I2, a vector diagram shown in FIG. 6C can be obtained.

As shown in FIG. 6C, the tube 2, the metal markers 51a and 52a, and the metal markers 51a and 52a in the captured image P have a relationship of external division points. That is, the metal marker 51a in the captured image P is a point at which a line segment SM1 formed by the tube 2 and the metal marker 51a is externally separated at a ratio of t1:(1−t1). The metal marker 52a in the captured image P is a point at which a line segment SM2 formed by the tube 2 and the metal marker 52a is externally separated at a ratio of t2:(1−t2). From the above relationship, the following Equations (1) and (2) are obtained.

$$\vec{S}*t1+\vec{M}1*(1-t1)=\vec{I}1 \tag{1}$$

$$\vec{S}*t2+\vec{M}2*(1-t2)=\vec{I}2 \tag{2}$$

Here, the position coordinates of the position S of the tube 2 are defined as (x, y, Sd). The position coordinates of the position M1 of the metal marker 51a are defined as (Pa, Pb, Pd+Ps). The position coordinates of the position M2 of the metal marker 52a are defined as (Pa, Pb, Pd). The position coordinates of the position I1 of the metal marker 51a in the captured image P are defined as (a1, b1, 0). The position coordinates of the position of the metal marker 52a in the captured image P are defined as (a2, b2, 0).

x is the coordinate of the tube 2 in the X direction. y is the coordinate of the tube 2 in the Y direction. Pa is the coordinates of the metal markers 51a and 52a in the X direction. Pb is the coordinates of the metal markers 51a and 52a in the Y direction. Sd is a distance (source image receptor distance: SID) from the detector 4 to the tube 2 in the Z direction. Pd is a distance from the detector 4 to the metal marker 52a in the Z direction. Ps is a distance between the metal marker 51a and 52a in the Z direction.

From the position coordinates of the tube 2, the position coordinates of the metal markers 51a and 52a, the position coordinates of the metal markers 51a and 52a in the captured image P, and the above Equations (1) and (2), the following Equations (3) to (8) are obtained.

$$x*t1+Pa*(1-t1)=a1 \tag{3}$$

$$x*t2+Pa*(1-t2)=a2 \tag{4}$$

$$y*t1+Pa*(1-t1)=b1 \tag{5}$$

$$y*t2+Pa*(1-t2)=b1 \tag{6}$$

$$Sd*t1+(Pd+Ps)*(1-t1)=0 \tag{7}$$

$$Sd*t2+Pd*(1-t2)=0 \tag{8}$$

In the above Equations (3) to (8), Sd, Pd, and Ps are known values. Therefore, since the number of unknowns and the number of Equations are equal, the position information of the tube 2 can be acquired. Specifically, the following Equations (9) and (10) are obtained from Equations (7) and (8).

$$t1 = \frac{Pd + Ps}{Pd + Ps - Sd} \tag{9}$$

$$t2 = \frac{Pd}{Pd - Sd} \tag{10}$$

Here, assuming that the solution of the above Equation (9) is t1=α and the solution of the above Equation (10) is t2=β, the following Equation (11) is obtained from the above Equations (1) and (2). In addition, the following Equation (12) is obtained from the above Equations (3) and (4).

$$x = \frac{a1*(1-\beta)-a2*(1-\alpha)}{\beta-\alpha} \tag{11}$$

$$y = \frac{b1*(1-\beta)-b2*(1-\alpha)}{\beta-\alpha} \tag{12}$$

a1 and a2 in the above Equation (11) are obtained by acquiring the values of the X coordinates of the metal markers 51a and 52a in the captured image P. b1 and b2 in the above Equation (12) are obtained by acquiring the values of the Y coordinates of the metal markers 51a and 52a in the captured image P. Therefore, the radiation image processing apparatus 6 can acquire the position information of the tube 2 at the time of capturing of the captured image P from the coordinate values of the metal markers 51a and 52a in the captured image P and the above Equations (11) and (12).

(Estimation of the Position of a Tube)

Next, processing of the radiation image processing apparatus 6 will be described with reference to FIG. 7. FIG. 7 is a flowchart illustrating the flow of tube position estimation processing of the radiation image processing apparatus 6.

As shown in FIG. 7, the radiation image processing apparatus 6 executes a step S1 of creating a binarized image, a step S2 of labeling, a step S3 of calculating the area of each region, a step S4 of determining the distance of a marker based on the area, a step S5 of marker pair determination, and a step S6 of tube coordinate estimation in this order.

The step S1 of creating a binarized image is a step in which the image generation unit 61 generates a binarized image P based on the signal of the image detected by the detector 4.

The step S2 of labeling is a step in which the label processing unit 62a performs labeling on each of the metal markers 51a to 51d and 52a to 52d in the captured image P so that the metal markers 51a to 51d and 52a to 52d are distinguished from each other. Here, for example, with a rectangular region of a central portion of the binarized captured image P as a region of interest (observed region), a region where pixels having the same pixel value (pixels where adjacent pixels have the same pixel value) are continuous is extracted by labeling processing on the region of interest and the same label is assigned to the region, so that the image region of the phantom including the metal markers is distinguished from the image region of the subject T.

The feature amount may be extracted based on the average value of the pixel values of pixels, which form the region of interest, to distinguish the subject T and the metal markers from each other.

The step S3 of calculating the area of each region is a step in which the group processing unit 62b calculates the area of each of the plurality of metal markers 51a to 51d and 52a to 52d in the captured image P labeled by the label processing unit 62a. In step S3 of calculating the area of each region, the group processing unit 62b also calculates an average value of the maximum value and the minimum value of the calculated area.

The step S4 of determining the distance of a marker based on the area is a step in which, with the calculated average value as a threshold value, the group processing unit 62b determines that the metal markers 51a to 51d each having an area larger than the average value, in the captured image P, are relatively far (located in an upper portion within the phantom 5 shown in FIG. 2) from the detector 4 and classifies the metal markers 51a to 51d into the first group and determines that the metal markers 52a to 52d each having an area smaller than the average value in the captured image P are relatively close (located in a lower portion within the phantom 5 shown in FIG. 2) to the detector 4 and classifies the metal markers 52a to 52d into the second group.

The step S5 of marker pair determination is a step in which the marker classification unit 62c classifies the plurality of metal markers 51a to 51d and 52a to 52d based on the relative positions of the plurality of metal markers 51a to 51d and 52a to 52d on the xy coordinate plane for each of the groups classified by the group processing unit 62b and the pair processing unit 62d selects the metal markers 51a to 51d of the first group and the metal markers 52a to 52d of the second group, of which the relative positions match each other, as a pair.

Specifically, as described with reference to (A) and (B) of FIG. 5, for example, a pair of the metal marker 51a and the metal marker 52a, a pair of the metal marker 51b and the metal marker 52b, a pair of the metal marker 51c and the metal marker 52c, or a pair of the metal marker 51d and metal marker 52d is selected as metal markers whose relative positions match each other.

In the phantom 5, as a plurality of metal markers that form pairs by being disposed so as to be separated in the distance direction with respect to the detector T, the number capable of forming four pairs is exemplified herein. However, the present invention is not limited thereto. For example, even though a case where some metal markers do not appear in the captured image due to the phantom 5 being tilted is taken into consideration, a number of metal markers capable of forming at least two pairs may be provided for the estimation of the tube position. In addition, the markers are not limited to metal, and any material may be used as long as the amount of absorption of X-rays is large.

The step S6 of tube coordinate estimation is a step in which the tube position estimation processing unit 63 estimates the position of the tube 2 based on the position coordinates of the metal markers 51a to 51d and 52a to 52d selected as pairs by the pair processing unit 62d using the method described with reference to FIGS. 6A, 6B, and 6C.

(Effects of the Embodiment)

According to the embodiment of the present invention, the following effects can be obtained.

In the present embodiment, as described above, the radiation image processing apparatus 6 is a radiation image processing apparatus including the detector 4 that is disposed so as to face the tube 2, which is a movably held radiation source, and converts the captured image P by radiation emitted from the tube 2 into image data and the phantom 5 that is provided between the tube 2 and the detector 4 and has a plurality of metal markers 51a to 51d and 52a to 52d disposed so as to be separated in the distance direction with respect to the detector 4. The radiation image processing apparatus 6 includes: the group processing unit 62b that classifies the plurality of metal markers 51a to 51d and 52a to 52d into the first group relatively far from the detector 4 and the second group relatively close to the detector 4 based on the area of each image of the plurality of metal markers 51a to 51d and 52a to 52d in the captured image P; the marker classification unit 62c that classifies the plurality of metal markers 51a to 51d and 52a to 52d based on the relative positions of the plurality of metal markers 51a to 51d and 52a to 52d on the image plane of the captured image P for each of the classified groups; and the pair processing unit 62d that selects the metal markers 51a to 51d of the first group and the metal markers 52a to 52d of the second group, of which the relative positions match each other, as a pair.

In this manner, the plurality of metal markers 51a to 51d and 52a to 52d in the captured image P can be selected as pairs after being separated in the distance direction with respect to the detector 4. Therefore, it is possible to estimate the position of the tube 2 at the time of imaging based on the positions of the plurality of pairs of metal markers 51a to 51d and 52a to 52d in the captured image P. As a result, for example, even in a case where the phantom 5 is inclined, it is possible to correctly estimate the position of the tube 2 at the time of imaging. That is, it is possible to accurately estimate the position of the tube 2 at the time of imaging.

In the present embodiment, the radiation image processing apparatus 6 includes the tube position estimation processing unit 63 that estimates the position of the tube 2 based on the position coordinates of the metal markers 51a to 51d and 52a to 52d selected as pairs by the pair processing unit 62d.

Then, in the present embodiment, the marker classification unit 62c classifies the plurality of metal markers 51a to 51d and 52a to 52d based on the position from the centers of gravity G1 and G2 by using the central point of a region surrounded by the metal marker located in the outermost portion in one direction on the image plane of the captured image P and the metal marker located in the outermost portion in a direction perpendicular to the one direction as the centers of gravity G1 and G2.

In the present embodiment, the plurality of metal markers 51a to 51d and 52a to 52d are a number of metal markers that can form at least two pairs from the metal markers 51a to 51d of the first group and the metal markers 52a to 52d of the second group.

In the present embodiment, a radiation image processing method is a radiation image processing method in the radiation image processing apparatus 6 including the detector 4 that is disposed so as to face the tube 2, which is a movably held radiation source, and converts the captured image P by radiation emitted from the tube 2 into image data and the phantom 5 that is provided between the tube 2 and the detector 4 and has a plurality of metal markers 51a to 51d and 52a to 52d disposed so as to be separated in the distance direction with respect to the detector 4. The radiation image processing method includes: a group processing step of classifying the plurality of metal markers 51a to 51d and 52a to 52d into the first group relatively far from the detector 4 and the second group relatively close to the detector 4 based on the area of each image of the plurality of metal markers 51a to 51d and 52a to 52d in the captured image P; a marker classification step of classifying the plurality of metal markers 51a to 51d and 52a to 52d based on the relative positions of the plurality of metal markers 51a to 51d and 52a to 52d on the image plane of the captured image P for each of the classified groups; and a pair processing step of selecting the metal markers 51a to 51d of the first group and the metal markers 52a to 52d of the second group, of which the relative positions match each other, as a pair.

In the present embodiment, the radiation image processing method further includes a tube position estimation processing step of estimating the position of the tube 2 based on the position coordinates of the metal markers 51a to 51d and 52a to 52d selected as pairs in the pair processing step.

In the present embodiment, in the marker classification step, the plurality of metal markers 51a to 51d and 52a to 52d are classified based on the position from the centers of gravity G1 and G2 by using the central point of a region surrounded by the metal marker located in the outermost portion in one direction on the image plane of the captured image P and the metal marker located in the outermost portion in a direction perpendicular to the one direction as the centers of gravity G1 and G2.

In the present embodiment, the plurality of metal markers 51a to 51d and 52a to 52d are a number of metal markers 51a to 51d and 52a to 52d that can form at least two pairs from the metal markers 51a to 51d of the first group and the metal markers 52a to 52d of the second group.

(Modification Example)

The embodiment described above is to be considered in all respects as illustrative and not restrictive. The scope of the present invention is indicated not by the above description of the embodiment but by the scope of the claims, and further includes all changes (modification examples) within the meaning and scope equivalent to the scope of the claims.

For example, in the above embodiment, the phantom 5 has the metal marker 50. However, since the metal marker 50 is used to check whether or not the processing in the radiation image processing apparatus 6 is correct or for image reconstruction or the like, the phantom 5 may not have the metal marker 50.

What is claimed is:

1. A radiation image processing apparatus using a phantom, comprising:
    a tube configured to emit radiation and to scan the phantom;
    a detector that is disposed so as to face the tube, the detector being configured to detect the radiation emitted from the tube to obtain a captured image of the phantom when the tube scans the phantom, and convert the captured image into image data, wherein the phantom is provided between the tube and the detector, and the phantom has a plurality of markers as a first group at positions relatively far from the detector and has a plurality of markers as a second group at positions relatively close to the detector; and
    a processor configured to determine whether the plurality of markers in the captured image correspond to markers in the first group or markers in the second group based on an area of each of the plurality of markers in the captured image, and select, from the plurality of markers, a marker corresponding to the first group at the positions relatively far from the detector and a marker corresponding to the second group at the positions relatively close to the detector as a pair of markers based on a relative positional relationship between the plurality of markers in the captured image.

2. The radiation image processing apparatus according to claim 1,
    wherein the processor is further configured to estimate a position of the tube based on position coordinates of markers selected as the pair of markers.

3. The radiation image processing apparatus according to claim 1,
    wherein, by using a central point of a region surrounded by a marker located in an outermost portion in one direction on an image plane of the captured image and a metal marker located in an outermost portion in a direction perpendicular to the one direction as a center of gravity, the plurality of markers are classified based on a position from the center of gravity.

4. The radiation image processing apparatus according to claim 1,
    wherein the plurality of markers are a number of markers capable of forming at least two pairs from the markers of the first group and the markers of the second group.

5. A radiation image processing method in a radiation image processing apparatus including a tube that emits radiation, a detector that is disposed so as to face the tube, and that detects the radiation emitted from the tube to obtain a captured image and converts the captured image into image data, and a phantom that is provided between the tube and the detector, and the phantom has a plurality of markers as a first group at positions relatively far from the detector and has a plurality of markers as a second group at positions relatively close to the detector, the method comprising:
    scanning the phantom with radiation from the tube;
    obtaining a captured image of the phantom by detecting radiation with the detector;
    converting the captured image into image data;
    determining whether the plurality of markers in the captured image correspond to markers in the first group at the positions relatively far from the detector or markers in the second group at the positions relatively close to the detector based on an area of each of the plurality of markers in the captured image; and
    selecting, from the plurality of markers, a marker corresponding to the first group and a marker corresponding to the second group as a pair of markers based on a relative positional relationship between the plurality of markers in the captured image.

6. The radiation image processing method according to claim 5, further comprising:
    estimating a position of the tube based on position coordinates of markers selected as the pair of markers.

7. The radiation image processing method according to claim 5,
    wherein, by using a central point of a region surrounded by a marker located in an outermost portion in one direction on an image plane of the captured image and a metal marker located in an outermost portion in a direction perpendicular to the one direction as a center of gravity, the plurality of markers are classified based on a position from the center of gravity.

8. The radiation image processing method according to claim 5,
    wherein the plurality of markers are a number of markers capable of forming at least two pairs from the markers of the first group and the markers of the second group.

* * * * *